United States Patent
Griffin et al.

(10) Patent No.: US 9,102,951 B2
(45) Date of Patent: Aug. 11, 2015

(54) PROCESS FOR RECOVERING SALT DURING A LIGNOCELLULOSIC CONVERSION PROCESS

(75) Inventors: Robert Griffin, Ontario (CA); Ziyad Rahme, Ontario (CA); Patricia Dawn MacLean, Ontario (CA); Brian Foody, Ontario (CA)

(73) Assignee: IOGEN ENERGY CORPORATION, Ontario (CA)

( * ) Notice: Subject to any disclaimer, the term of this patent is extended or adjusted under 35 U.S.C. 154(b) by 0 days.

(21) Appl. No.: 14/241,133

(22) PCT Filed: Aug. 24, 2012

(86) PCT No.: PCT/CA2012/050589
§ 371 (c)(1),
(2), (4) Date: May 19, 2014

(87) PCT Pub. No.: WO2013/029171
PCT Pub. Date: Mar. 7, 2013

(65) Prior Publication Data
US 2014/0248676 A1    Sep. 4, 2014

Related U.S. Application Data

(60) Provisional application No. 61/529,274, filed on Aug. 31, 2011.

(51) Int. Cl.
| | | |
|---|---|---|
| C12P 3/00 | (2006.01) |
| F23G 5/04 | (2006.01) |
| C05D 9/00 | (2006.01) |
| F23G 7/10 | (2006.01) |
| C02F 9/00 | (2006.01) |
| C02F 1/52 | (2006.01) |
| C02F 1/04 | (2006.01) |
| D21C 11/00 | (2006.01) |
| B01D 3/00 | (2006.01) |
| C05F 5/00 | (2006.01) |
| F22B 1/18 | (2006.01) |
| C12P 7/10 | (2006.01) |
| C22B 26/22 | (2006.01) |

(52) U.S. Cl.
CPC . *C12P 3/00* (2013.01); *B01D 3/002* (2013.01); *C02F 1/04* (2013.01); *C02F 1/52* (2013.01); *C02F 9/00* (2013.01); *C05D 9/00* (2013.01); *C05F 5/008* (2013.01); *C12P 7/10* (2013.01); *C22B 26/22* (2013.01); *D21C 11/0007* (2013.01); *F22B 1/18* (2013.01); *F23G 5/04* (2013.01); *F23G 7/10* (2013.01); *Y02E 50/16* (2013.01); *Y02E 50/343* (2013.01)

(58) Field of Classification Search
CPC ............ B01D 1/00; B01D 3/00; B01D 3/001; B01D 3/002; B01D 11/02; B01D 11/028; B01D 11/0284; B01D 11/0288; B01D 17/00; B01D 17/08; B01D 17/10; B01D 37/00; B01D 21/01; C05D 9/00; C05F 5/008; C05F 11/00; C12P 3/00; C12P 7/06; C12P 7/08; C12P 7/10; F22B 1/00; F22B 1/18; F23G 5/04; F23G 7/10; F23G 7/105; F23G 5/00; F23G 5/006; F23G 5/008; F23G 5/44; F23G 5/446; F23G 7/00; F23G 7/04; F23G 2201/10; F23G 2201/20; C02F 1/04; C02F 1/52; C02F 1/5236; Y02E 50/16; Y02E 50/543; D21C 11/0007; C22B 26/10; C22B 26/22
USPC ...................... 44/307, 605; 71/11, 23, 26, 31; 159/47.1; 127/34, 36, 37, 46.1, 48, 53, 127/55, 58, 61; 203/39, 47; 210/632, 634, 210/702, 712, 770, 774, 806; 110/341, 346; 423/580.1, 158, 184, 499.5; 435/136, 435/161, 163, 165
See application file for complete search history.

(56) References Cited

U.S. PATENT DOCUMENTS

| | | |
|---|---|---|
| 3,411,465 A | 11/1968 | Shirai |
| 3,902,859 A | 9/1975 | Greco |
| 3,925,028 A | 12/1975 | Lozano |
| 4,164,507 A | 8/1979 | Blytas et al. |
| 4,604,957 A * | 8/1986 | Cederquist .................... 110/238 |

| | | | |
|---|---|---|---|
| 5,138,982 A * | 8/1992 | Ohshita et al. | 122/4 D |
| 5,141,732 A | 8/1992 | Haardt et al. | |
| 5,177,008 A * | 1/1993 | Kampen | 435/139 |
| 5,967,095 A * | 10/1999 | Greves | 119/795 |
| 7,569,146 B2 * | 8/2009 | Peyton et al. | 210/603 |
| 8,617,281 B2 * | 12/2013 | Aharon et al. | 71/12 |
| 2002/0130089 A1 * | 9/2002 | Temple et al. | 210/727 |
| 2003/0050520 A1 | 3/2003 | Ahern | |
| 2006/0057264 A1 * | 3/2006 | Hughes et al. | 426/495 |
| 2008/0102502 A1 * | 5/2008 | Foody et al. | 435/161 |
| 2009/0008235 A1 * | 1/2009 | Goel et al. | 203/41 |
| 2009/0035826 A1 * | 2/2009 | Tolan et al. | 435/99 |
| 2009/0056707 A1 * | 3/2009 | Foody et al. | 127/46.2 |
| 2009/0263540 A1 | 10/2009 | Allen et al. | |
| 2009/0286295 A1 * | 11/2009 | Medoff et al. | 435/162 |
| 2011/0003352 A1 * | 1/2011 | Retsina et al. | 435/136 |
| 2011/0056126 A1 * | 3/2011 | Harvey et al. | 44/606 |
| 2011/0067829 A1 | 3/2011 | Foan et al. | |
| 2011/0314726 A1 * | 12/2011 | Jameel et al. | 44/451 |
| 2012/0145094 A1 | 6/2012 | Simard | |
| 2014/0123973 A1 * | 5/2014 | North | 127/37 |

FOREIGN PATENT DOCUMENTS

| | | |
|---|---|---|
| CA | 2 562 467 | 10/2005 |
| CA | 2565422 A1 | 12/2005 |
| CA | 2580226 A1 | 4/2006 |
| CA | 2565433 A1 | 4/2008 |
| CA | 2786949 A1 | 8/2011 |
| CN | 1964767 | 5/2007 |
| CN | 101375863 | 3/2009 |
| EP | 0126058 B1 | 11/1984 |
| EP | 0 183 678 | 6/1986 |
| WO | 00/29666 A1 | 5/2000 |
| WO | 2005/099854 A1 | 10/2005 |
| WO | 2009/024100 A2 | 2/2009 |
| WO | 2009/058276 A1 | 5/2009 |
| WO | 2009/134745 A2 | 11/2009 |
| WO | 2009/146526 A1 | 12/2009 |
| WO | 2010/129637 A1 | 11/2010 |
| WO | 2010/135366 A1 | 11/2010 |
| WO | 2011/028554 A1 | 3/2011 |
| WO | 2011/047046 A1 | 4/2011 |

OTHER PUBLICATIONS

Publication by C.A. Cardona Alzate et al, "Energy consumption analysis of integrated flowsheets for production of fuel ethanol from lignocellulosic biomass", Published in 'Energy' vol. 31, (2006), pp. 2447-2459.*

Publication by V. Dornburg et al, "Economics and GHG emission reduction of a PLA bio-refinery system-Combining bottom-up analysis with price elasticity effects", Published in Resources, Conservation and Recycling 46 (2006), pp. 377-409.*

Aden et al., "Lignocellulosic Biomass to Ethanol Process Design and Economics Utilizing Co-Current Dilute Acid Prehydrolysis and Enzymatic Hydrolysis for Corn Stover", NREL/TP-510-32438, Jun. 2002.

Kazi et al., "Techno-Economic Analysis of Biochemical Scenarios for Production of Cellulosic Ethanol", NREL, NREL/TP-6A2-46588, Jun. 2010.

Larsson et al., "Recirculation of Process Water in the Production of Ethanol From Softwood", Bioresource Technology, vol. 60, No. 2 (1997) 143-51.

Taherzadeh et al, "Acid-Based Hydrolysis Processes for Ethanol from Lignocellulosic Materials: A Review", Bioethanol Review, BioResources, vol. 2, No. 3 (2007) 472-99.

Van Esch et al., "Ammonium Sulfate Crystallization—State of the Art and Trends". Proceedings of the 18th Symposium on Industrial Crystallization, vol. 2 (2008) 859-65.

Wilkie, et al., "Stillage characterization and anaerobic treatment of ethanol stillage from conventional and cellulosic feedstocks", Biomass & Bioenergy, vol. 19 (2000) 63-102.

Zhang et al., "A novel full recycling process through two-stage anaerobic treatment of distillery wastewater for bioethanol production from cassava", Journal of Hazardous Material, vol. 179 (2010) 635-41.

* cited by examiner

*Primary Examiner* — Joseph Drodge

(74) *Attorney, Agent, or Firm* — Fitzpatrick, Cella, Harper & Scinto

(57) ABSTRACT

The present invention relates to a process for generating steam and recovering salts during a lignocellulosic conversion process. The process comprises de-salting a still bottoms stream; incinerating a stream comprising lignin and the de-salted still bottoms stream in an incinerator; and utilizing the heat generated from said incinerating to produce steam. Further provided is a process that comprises feeding a concentrated still bottoms stream to a crystallizer and forming insoluble solids therein comprising salts. Furthermore, the invention relates to a process for recovering salts from a lignocellulosic conversion process, which process comprises the addition of solvent to a still bottoms stream to precipitate salts therefrom. Also provided is a still bottoms composition, a fertilizer product and a composition for incineration.

18 Claims, 3 Drawing Sheets

PROCESS FOR RECOVERING SALT DURING A LIGNOCELLULOSIC CONVERSION PROCESS

This application is a national stage application of PCT/CA2012/050589 having an international filing date of Aug. 24, 2012, which claims benefit of U.S. provisional application No. 61/529,274 filed Aug. 31, 2011, both of which are incorporated by reference herein.

TECHNICAL FIELD

The present invention relates to an improved process for recovering salts during a lignocellulosic conversion process. The present invention also relates to recovering salts and generating steam during a lignocellulosic conversion process.

BACKGROUND OF THE INVENTION

The production of fuel ethanol or other products from lignocellulosic feedstocks provides an attractive alternative to the fuel ethanol feedstocks used to date, such as corn, sugar cane and sugar beets. Cellulose is the most abundant natural polymer, comprising, on average, about one third of all plant matter. While many lignocellulosic materials, such as wood and cotton, are in high demand, other types have limited market value. These feedstocks are therefore potentially inexpensive and, as such, there is an untapped potential for their use as a source of ethanol. The lignocellulosic feedstocks that are the most promising for ethanol production include agricultural wastes, grasses, forestry wastes and sugar processing residues.

A series of chemical and biological treatments are commonly employed to convert the long chain polysaccharide sugars contained in the feedstock to shorter chain oligomers or monomers, which, in turn, are fermented to ethanol or other fermentation products. Such treatment stages may involve two primary processes, commonly referred to as pretreatment and enzymatic hydrolysis. The pretreatment may be effected by chemical addition, including acid, alkali, oxidizing agents or organic solvents, although hydrothermal pretreatments are known that employ hot water. If an acid pretreatment process is utilized, the feedstock may be subjected to steam and acid at a temperature, acid concentration, and length of time that are sufficient to hydrolyse a small portion of the cellulose to glucose and to hydrolyse the hemicellulose to xylose, arabinose, and other sugars monomers or oligomers, depending on the constituents of the hemicellulose.

Subsequent to an acid pretreatment reaction, the pretreated feedstock is quenched by the addition of a base, such as sodium hydroxide, ammonia or other base, and by lowering the stream temperature. This action also conditions the feedstock for the subsequent enzymatic hydrolysis stage. However, as a result of base addition (or acid addition if alkali pretreatment is employed), inorganic salts are produced, for example sulfate salts. This adds to the existing salt load resulting from the significant amounts of inorganic salts present in the feedstock itself and which are carried through to this stage of the process. The resultant high levels of salts originating from these sources can be problematic in downstream unit operations, as discussed below. Subsequent to pretreatment, the cellulose remaining in the pretreated feedstock is converted to monomeric glucose by the use of an enzymatic mixture, primarily composed of cellulase enzymes.

After the completion of the pretreatment and enzyme hydrolysis stages, the process stream is composed of a liquid phase containing the fermentable sugars and other water soluble compounds, including the salts that are carried through to this stream. The process stream also typically contains an insoluble solids phase, comprised of lignin and other insoluble components. Lignin is a bio-polymer that differs from cellulose and hemicellulose in that it is not composed of carbohydrates and therefore is not a source of fermentable sugar. The insoluble lignin rich fraction that remains may either be filtered out of the stream after enzymatic hydrolysis, or may be carried forward through subsequent processing steps. Regardless of the point at which the lignin is separated from the stream, the lignin rich solids may be used as a fuel material for a boiler system, which typically produces steam for either use in the process, including heat that may be used in the process, electricity production, building heating, or a combination thereof.

The stream leaving the enzyme hydrolysis stage, either with or without the insoluble lignin, is fed to a fermentation stage, which employs any of several microbial organisms to convert the glucose, xylose, arabinose, or any combination of these, into ethanol or other fermentation products. This stream is typically called fermentation beer. The fermentation beer may be fed to a distillation system that strips the ethanol out of the solution and the ethanol is then further processed as required for sale as a transportation fuel.

The residual liquid phase remaining after removal of alcohol by distillation or other means is typically called still bottoms, and contains a complex mixture of organic and inorganic components, derived from the process chemicals, biological treatment stages, and from the feedstock. For example, the still bottoms stream will generally contain large quantities of sulfate, or other conjugate base of the acid used in the pretreatment step, the cation of the base used for neutralization at the completion of pretreatment, various protein components, polyols, soluble lignin and lignin derived compounds, unfermented sugars, potassium salts, magnesium salts, chloride salts, and other trace inorganic species.

In the corn ethanol industry, the still bottoms stream is typically dried and blended with the residual grain material and sold as an animal feed. However, the composition of the still bottoms from the cellulose ethanol process may not be suitable for this market. Consequently, a disposal method that has been suggested for still bottoms derived from cellulosic conversion processes is biological waste water treatment. While biological waste water treatment of such still bottoms streams removes the organic constituents, many of the inorganic components either present processing difficulties, or pass through the system unaffected. The final effluent then contains a large quantity of dissolved salts which may not meet effluent discharge criteria, or may pose processing problems if the waste water effluent stream is recycled.

A known waste disposal technique is incineration, which allows the recovery of heat from the combustion of organics. However, the incineration of a still bottoms stream derived from cellulosic conversion processes is particularly challenging due to the presence of inorganic components such as sulfate, ammonium, potassium, chloride, and other elements. In particular, the sulfate will convert at least in part to sulfur oxides, and the ammonia will convert at least in part to nitrogen oxides, both of which are regulated pollutants, and will require additional equipment to control and reduce them to acceptable levels. Moreover, the potassium and chloride may cause a low melting point slag and possibly volatile fume that will foul components of the system and generate dust. While technically feasible, incineration of the still bottoms stream derived from cellulosic conversion processes presents several challenges that greatly increase the cost and complexity.

SUMMARY OF THE INVENTION

The present invention relates to an improved process for recovering salts during a lignocellulosic conversion process. The present invention also relates to a process for recovering salts and generating steam during a lignocellulosic conversion process.

The present invention provides a method to improve the incineration characteristics of a still bottoms stream by removing inorganic elements prior to routing the stream to an incinerator. The resultant de-salted still bottoms stream is particularly amenable to incineration and energy recovery operations. Furthermore, a stream comprising lignin isolated from the process is combusted in the incinerator. Advantageously, the heat generated from combusting both streams generates heat energy in the form of steam for use in the process or elsewhere.

Significant capital expense savings, process simplification and intensification are potentially achieved by incinerating the de-salted still bottoms stream and the lignin stream in one system. Process simplification provides the advantage of fewer systems to purchase and manage. For example, according to embodiments of the invention, one energy recovery and steam production system may be employed, which simplifies the overall energy distribution and integration for the entire facility. Moreover, the process of the present invention may potentially only require one pollution abatement system for control of residual sulfur oxides, nitrogen oxides, dust, and other regulated pollutants.

According to a first aspect of the invention, there is provided a process for generating steam and recovering salts during a lignocellulosic conversion process. The process comprises the steps of: (i) obtaining a stream comprising lignin and a still bottoms stream generated during the lignocellulosic conversion process; (ii) removing at least a portion of the water from the still bottoms stream to produce a concentrated still bottoms stream; (iii) removing at least a portion of the salts from the concentrated still bottoms stream to produce a de-salted still bottoms stream; (iv) incinerating the stream comprising lignin and the de-salted still bottoms stream in an incinerator; and (v) utilizing the heat generated from the incinerating to produce steam.

According to some embodiments of the invention, between about 10 and about 90%, or between about 30 and about 90% of the water is removed from the still bottoms stream to produce the concentrated still bottoms stream. The step of removing water from the still bottoms may comprise evaporation.

According to further embodiments of the invention, the step of removing at least a portion of the salts from the concentrated still bottoms stream comprises one or more steps of precipitating salts from the concentrated still bottoms stream by use of a solvent. This may comprise the addition of an alcohol. The alcohol may be methanol, butanol, ethanol, propanol or isopropanol. Preferably, the solvent is methanol or ethanol. The alcohol may be recovered and recycled.

According to further embodiments of the invention, a fertilizer is produced from the salts removed from the concentrated still bottoms.

In further embodiments, the stream comprising lignin is obtained from a lignin separation process conducted after a step of enzymatic hydrolysis to produce glucose from cellulose conducted during said lignocellulosic process. The stream comprising lignin may also be obtained from a lignin separation process conducted after a step of fermentation to produce the fermentation product. Without being limiting, the stream comprising lignin may also be obtained from a lignin separation process conducted after distillation to separate the ethanol product. For example, the lignin separation process may be conducted on a still bottoms stream. The lignin separation process may include a filter press operation.

According to some embodiments of the invention, the incinerator is a boiler, for example, a bubbling fluidized bed.

The lignocellulosic conversion process may produce ethanol.

The present invention relates, in a further aspect, to the application of a particularly suitable method to achieve the removal of the problematic inorganic elements for use as a fertilizer. Such method involves feeding a concentrated still bottoms stream to a crystallizer; forming insoluble solids in the crystallizer by the addition of alcohol; producing a fertilizer from the insoluble solids; recovering the alcohol in one or more stages, thereby producing recovered alcohol; and recycling the recovered alcohol in the process.

The precipitated salts obtained from the foregoing process may be largely comprised of the inorganic elements contained in the feedstock and the process chemicals used in previous steps. The salts can be used as a fertilizer constituent, which will improve the economics of the overall cellulose ethanol process.

According to embodiments of the foregoing aspect of the invention, the stream comprising lignin is obtained from the process and combusted in an incinerator. In further embodiments, the insoluble solids are dried prior to the step of producing a fertilizer. The fertilizer may comprise mixed salts. For example, the mixed salts may at least partially be composed of struvite.

According to a further aspect of the invention, there is provided a process for obtaining salt from a still bottoms stream resulting from a lignocellulosic conversion process to produce an alcohol, said process comprising the steps of: (i) processing a lignocellulosic feedstock to produce fermentable sugar; (ii) fermenting the sugar with microorganisms to produce a fermentation broth comprising alcohol; (iii) recovering the alcohol from the fermentation broth in one or more stages to produce an alcohol-enriched mixture and the still bottoms stream that comprises one or more salts; and (iv) recovering the one or more salts by precipitation with alcohol.

According to a further aspect of the invention, there is provided a still bottoms composition resulting from a lignocellulosic conversion process, said composition comprising an aqueous component, a solvent that is soluble in water and insoluble solids comprising at least inorganic salts originating from the lignocellulosic feedstock and optionally inorganic salts originating from the addition of acid or alkali during said lignocellulosic conversion process. Furthermore, the present invention relates to a fertilizer product isolated from the foregoing still bottoms composition.

Further provided is a composition for incineration resulting from a lignocellulosic conversion process, said composition comprising de-salted still bottoms and lignin.

DETAILED DESCRIPTION OF THE INVENTION

Figure 1A:
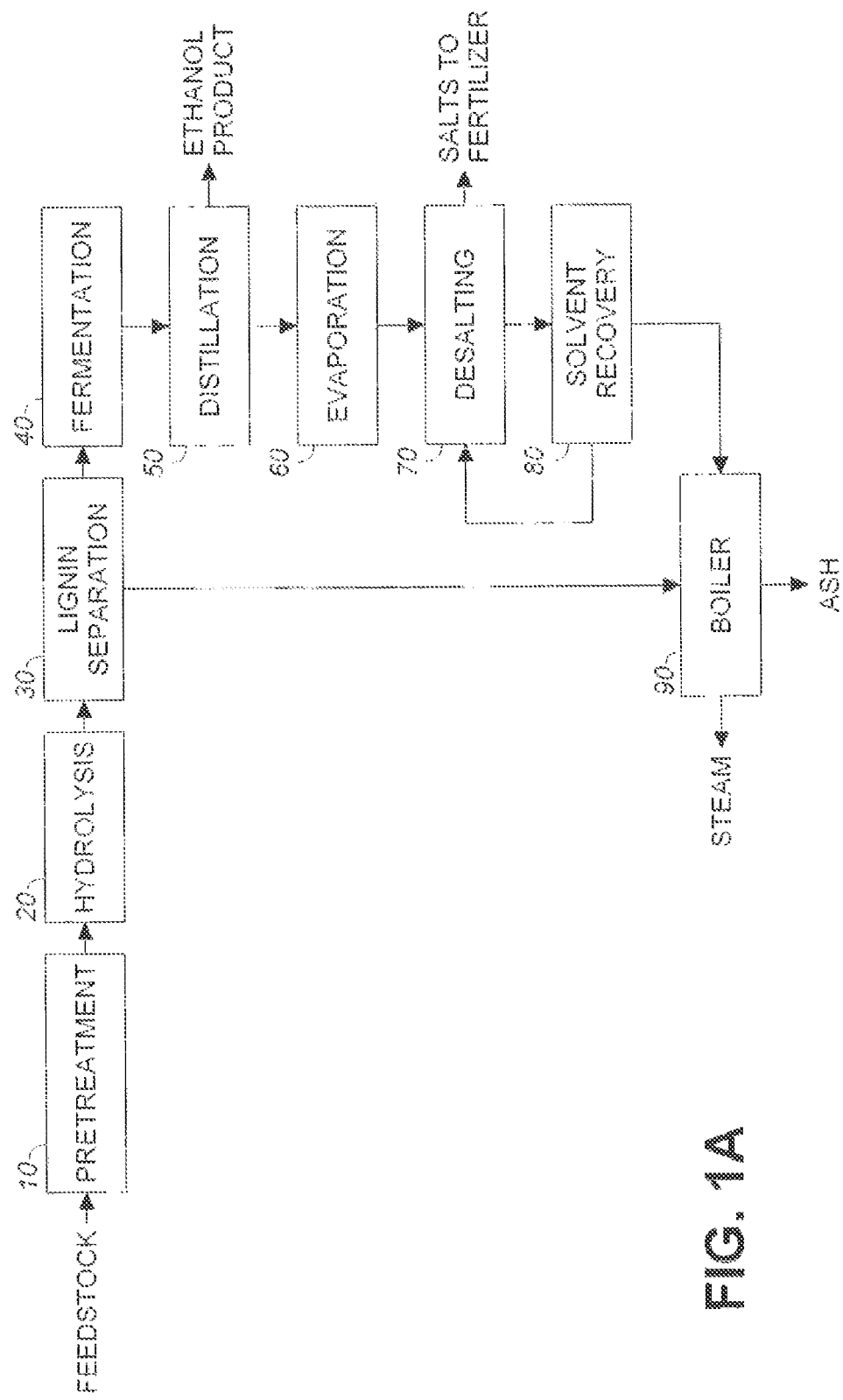
FIG. 1A is a process flow diagram depicting an embodiment of the invention in which a lignin stream is isolated after hydrolysis and combined with a de-salted still bottoms stream to produce a combined stream that is combusted to generate steam.

The following description is of a preferred embodiment by way of example only and without limitation to the combination of features necessary for carrying the invention into effect. The headings provided are not meant to be limiting of the various embodiments of the invention. Terms such as "comprises", "comprising", "comprise", "includes", "including" and "include" are not meant to be limiting. In addition, the use of the singular includes the plural, and "or" means "and/or" unless otherwise stated. Unless otherwise defined herein, all technical and scientific terms used herein have the same meaning as commonly understood by one of ordinary skill in the art.

Description of Feedstock Types

By the term "lignocellulosic conversion process", it is meant any process for producing a chemical product from a lignocellulosic feedstock, including, but not limited to ethanol. The chemical product may be a fermentation product produced by fermentation of sugar or a chemical produced from sugar by non-biological means.

By the term "lignocellulosic feedstock", it is meant any type of plant biomass such as, but not limited to, plant biomass, cultivated crops such as, but not limited to grasses, for example, but not limited to, C4 grasses, such as switch grass, cord grass, rye grass, miscanthus, reed canary grass, or a combination thereof, sugar processing residues, for example, but not limited to, baggase, such as sugar cane bagasse, beet pulp, or a combination thereof, agricultural residues, for example, but not limited to, soybean stover, corn stover, rice straw, sugar cane straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the lignocellulosic feedstock may comprise lignocellulosic waste material or forestry waste materials such as, but not limited to, newsprint, cardboard and the like. Lignocellulosic feedstock may comprise one species of fiber or, alternatively, lignocellulosic feedstock may comprise a mixture of fibers that originate from different lignocellulosic feedstocks.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or any amount therebetween. Such feedstocks also comprise hemicellulose, including xylan, arabinan, mannan and galactan. Furthermore, the lignocellulosic feedstock comprises lignin in an amount greater than about 10%, more typically in an amount greater than about 15% (w/w). The lignocellulosic feedstock may also comprise small amounts of sucrose, fructose and starch, as well as acetate, silica, protein and inorganic salts, including salts of potassium, calcium, magnesium, sodium, manganese and iron. The salts may exist as carbonate, phosphate, chloride or other common salt forms.

Feedstock Size Reduction and Slurry Preparation

The lignocellulosic feedstock is generally first subjected to size reduction by methods including, but not limited to, milling, grinding, agitation, shredding, compression/expansion, or other types of mechanical action. The lignocellulosic feedstock from the size reduction process may produce a size-reduced feedstock comprising particles of a defined length. For example, at least 90% by weight of the particles in the size reduced feedstock may have a length less than between about ⅛ and about 8 inches. As would be appreciated by those of ordinary skill in the art, lignocellulosic feedstock that has been subjected to size reduction comprises feedstock particles having a range of sizes and shapes.

The feedstock is optionally slurried. Slurrying of the feedstock allows it to be pumped readily and may be carried out in any suitable batch or continuous mixing vessel, including a standpipe or pulper. Slurrying may be distinct from the water and chemical addition or may occur simultaneously therewith.

Slurrying can occur at any suitable consistency selected by those of ordinary skill in the art. However, in practice, the consistency of the incoming feedstock slurry utilized will depend on the specific mixing means employed and the specific pumps used. In one embodiment of the invention, the consistency of the feedstock slurry is between about 2% and about 40% (w/w) or more typically between about 4% and about 30% (w/w).

Pretreatment of the Lignocellulosic Feedstock

The lignocellulosic feedstock may be pretreated by reacting it under conditions that disrupt the fiber structure and that increase the susceptibility or accessibility of cellulose within the cellulosic fibers for subsequent conversion steps, such as enzymatic hydrolysis. In one embodiment of the invention, the pretreatment is performed so that a high degree of hydrolysis of the hemicellulose and only a small amount of conversion of cellulose to glucose occurs. The cellulose may be hydrolysed to glucose in a subsequent step that uses cellulase enzymes.

For acid pretreatment, the pH is typically between about 0.4 and about 3.5, or any pH therebetween. Acid pretreatment is preferably carried out at a maximum temperature of about 160° C. to about 280° C., or any temperature therebetween. The time that the feedstock is held at this temperature may be about 6 seconds to about 3600 seconds, or any time therebetween. The pretreatment is typically carried out under pressure. For example, the pressure during pretreatment may be between about 50 and about 920 psig, or any pressure range therebetween. The feedstock may be heated with steam during or prior to pretreatment.

The acid pretreatment produces a composition comprising an acid pretreated feedstock. Sugars produced by the hydrolysis of hemicellulose during acid pretreatment include xylose, glucose, arabinose, mannose, galactose or a combination thereof.

Pretreatment may also be carried out under alkaline conditions. Examples of suitable alkaline pretreatment processes include ammonia fiber expansion (AFEX) or dilute ammonia pretreatment. Other pretreatment methods include mechanical and hydrothermal pretreatment and pretreatment with organic solvents (known in the industry as Organosolv™ pretreatment).

According to one exemplary embodiment of the invention, the soluble components of the pretreated feedstock composition are separated from the solids. The aqueous stream, which includes the sugars released during pretreatment, the pretreatment chemical and other soluble components, may then be fermented using a microorganism capable of fermenting the sugars derived from the hemicellulose component of the feedstock.

Subsequent to pretreatment, the pretreated feedstock slurry is typically cooled to decrease its temperature to a range at which the cellulase enzymes are active. It should be appreciated that cooling of the feedstock can occur in a number of stages utilizing flashing, heat exchange or other suitable means.

Enzymatic Hydrolysis

The hydrolysis of the cellulose to soluble sugars can be carried out with any type of cellulase enzymes suitable for such purpose and effective at the pH and other conditions utilized, regardless of their source. Among the most widely studied, characterized and commercially produced cellulases are those obtained from fungi of the genera *Aspergillus*, *Humicola*, *Chrysosporium*, *Melanocarpus*, *Myceliophthora*, *Sporotrichum* and *Trichoderma*, and from the bacteria of the genera *Bacillus* and *Thermobifida*. The conversion of cellobiose to glucose is carried out by the enzyme β-glucosidase. By the term "β-glucosidase", it is meant any enzyme that hydrolyses the glucose dimer, cellobiose, to glucose.

An appropriate cellulase dosage can be about 1.0 to about 40.0 Filter Paper Units (FPU or IU) per gram of cellulose, or any amount therebetween. The FPU is a standard measurement familiar to those skilled in the art and is defined and measured according to Ghose (Pure and Appl. Chem., 1987, 59:257-268; which is incorporated herein by reference). A preferred cellulase dosage is about 10 to 20 FPU per gram cellulose, or any amount therebetween.

The enzymatic hydrolysis is generally conducted at a pH between about 4.0 and 6.0, or any pH therebetween, as this is within the optimal pH range of most cellulases. If acid pretreatment is utilized, the pH of the feedstock will be increased with alkali to about pH 4.0 to about 6.0, or any pH therebetween. prior to enzymatic hydrolysis, or more typically between about 4.5 and about 5.5, or any pH therebetween. However, cellulases with pH optima at more acidic and more alkaline pH values are known. As discussed below, the addition of alkali at this stage of the process produces salts that can be recovered for use as a fertilizer, depending on the identity of the alkali used in the process.

The temperature of the slurry is adjusted so that it is within the optimum range for the activity of the cellulase enzymes. Generally, a temperature of about 45° C. to about 70° C., or any temperature therebetween, or about 45° C. to about 65° C., or any temperature therebetween, is suitable for most cellulase enzymes. However, the temperature of the slurry may be higher for thermophilic cellulase enzymes.

The hydrolysis may be conducted simultaneously with fermentation in a simultaneous saccharification and fermentation, also referred to as "SSF". SSF is typically carried out at temperatures of 35 to 38° C., or any temperature therebetween, which is a compromise between, for example, a 50° C. optimum for cellulase and a 28° C. optimum for yeast.

The stream resulting from hydrolysis typically comprises soluble process chemicals, salts, proteins, and other organics derived from the feedstock, and an insoluble solids phase, comprised of lignin, unreacted polysaccharide, and other water insoluble components. Lignin may be separated from the hydrolysate at this stage of the process and fed to the incinerator, as discussed below. It should be understood that the other solids may be carried forward in the lignin separation, including the unconverted polysaccharide and other water insoluble components. The lignin material may or may not be washed to recover additional sugars and to remove process chemicals.

Fermentation

Subsequent to enzymatic hydrolysis, fermentation of the glucose may be carried out to produce ethanol or other fermentation products. The fermentation of ethanol is typically carried out with a *Saccharomyces* spp. yeast. Glucose and any other hexoses present in the sugar stream may be fermented to ethanol by wild-type *Saccharomyces cerevisiae*, although genetically modified yeasts may be employed as well, as discussed below. The ethanol is distilled to obtain a concentrated ethanol solution.

The fermentation is typically conducted at a pH between about 4.0 and about 6.0, or any pH therebetween, or between about 4.5 and about 6.0, or any pH therebetween. To attain the foregoing pH range for fermentation, it may be necessary to add alkali to the fermentation sugar feed stream. The fermentation sugar feed stream will comprise one or more sugar monomers derived from cellulose, hemicellulose or both polymeric components. Sugar monomers derived from cellulose include glucose, while hydrolysis of the hemicellulose component yields such sugars as xylose, glucose, arabinose, mannose, galactose, or a combination thereof.

Xylose and arabinose that are derived from the hemicellulose may also be fermented to ethanol by a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (U.S. Pat. Nos. 5,789,210, 5,866,382, 6,582,944 and 7,527,927 and European Patent No. 450,530) or (b) fungal or bacterial xylose isomerase (XI) gene (U.S. Pat. Nos. 6,475,768 and 7,622,284). Examples of yeasts that have been genetically modified to ferment L-arabinose include, but are not limited to, recombinant *Saccharomyces* strains into which genes from either fungal (U.S. Pat. No. 7,527,951) or bacterial (WO 2008/041840) arabinose metabolic pathways have been inserted.

In practice, the fermentation is typically performed at or near the temperature and pH optimum of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The dose of the fermentation microorganism will depend on other factors, such as the activity of the fermentation microorganism, the desired fermentation time, the volume of the reactor and other parameters. These parameters may be adjusted as desired to achieve optimal fermentation conditions.

The fermentation may also be supplemented with additional nutrients required for the growth of the fermentation microorganism. For example, yeast extract, specific amino acids, phosphate, nitrogen sources, salts, trace elements and vitamins may be added to the fermentation sugar feed stream to support their growth.

Recovery of the Fermentation Product or Other Chemical Product

The chemical product produced by the lignocellulosic conversion process may be recovered by any suitable technique. The residue remaining after recovery of the chemical is referred to herein as "still bottoms" or a "still bottoms stream".

A conventional technique for recovering ethanol is distillation. As used herein, the term "distillation" also encompasses steam and vacuum stripping.

The fermentation beer that is sent to distillation is a dilute ethanol solution. Microorganisms are potentially present depending upon whether or not they are removed from the beer by filtration or other means prior distillation of the beer.

The beer may additionally contain any components added during the fermentation to support growth of the microorganisms. The beer will also contain any organics that have not been consumed by the microorganisms, along with soluble and insoluble inorganic salts.

The beer is pumped through one or more distillation columns to separate the ethanol from the other components in the beer. The column(s) in the distillation unit is preferably operated in a continuous mode, although it should be understood that batch processes are also encompassed by the present invention. Furthermore, the column(s) may be operated at any desired pressure or vacuum. Heat for the distillation process may be added at one or more points either by direct steam injection or indirectly via heat exchangers. The distillation unit may contain one or more separate beer and rectifying columns, or a distillation column may be employed that comprises an integral enriching or rectification section. The ethanol vapour is further purified to fuel grade ethanol specification by removing residual water vapour by any of several well known techniques.

The still bottoms will contain a mixture of organic and inorganic components, derived from the process chemicals, biological treatment stages, and from the feedstock. For example, the still bottoms stream will generally contain large quantities of sulfate, or other conjugate base of the acid used in the pretreatment step, the cation of the base used for neutralization at the completion of pretreatment, various protein components, polyols, soluble lignin and lignin derived compounds, unfermented sugars, and inorganic salts, such as potassium salts, magnesium salts, chloride salts, and other trace inorganic species. This includes lignin and other unconverted solids if these components are not removed in upstream stages of the process. The still bottoms withdrawn from the beer column, or from a distillation column that comprises an integral enriching or rectification section, may be fed to a lignin separation unit, as discussed below.

The ethanol vapor is further purified to fuel grade specification by removing residual water vapor by any of several well known techniques.

Lignin Separation

The lignin that is sent to the incinerator may be obtained from any stage of the lignocellulosic conversion process, typically after the pretreatment. It should be understood that unconverted cellulose and other insoluble components may be carried forward with the lignin during the lignin separation. Without being limiting, streams from which the lignin can be separated include the hydrolysate stream comprising glucose resulting from enzymatic hydrolysis, the fermentation beer stream or the still bottoms stream remaining after distillation.

The lignin may be separated using conventional solid-liquid separation techniques prior to any further processing. Such separation techniques may include the use of pressure or vacuum filters, centrifugal filters or centrifuges, membrane filtration systems or gravity settlers. The solids content of the lignin stream resulting from the separation is typically greater than 30 wt %, more typically greater than 50 wt %. The separated solids comprising lignin are then fed to the incinerator to generate steam, as discussed below. The lignin material may or may not be washed to recover additional sugars and to remove process chemicals.

Without being limiting, a particularly suitable device for lignin separation is a lignin filter press. According to such embodiment, an incoming stream containing lignin and other undissolved solids is fed to a feed tank and then pumped to the lignin press where dewatering occurs. A lignin cake is produced that is then sent to the incinerator. The pressate from the filter press can then be fed to a pressate tank and concentrated further as discussed below.

Still Bottoms Concentration

The still bottoms contain inorganic salts that can be recovered as fertilizer and removal of water from the still bottoms can allow for more efficient removal of the salts. In some embodiments of the invention, between about 10% and about 90% (w/w), or any amount therebetween, or between about 30% and about 90% (w/w) or any amount therebetween, of the water is removed from the still bottoms prior to removal of the salts.

Concentration of the still bottoms may be carried out by evaporation, centrifugation, membrane separation or other suitable techniques. If the still bottoms are subjected to the lignin separation step, the liquid component of the still bottoms is concentrated and the salts are removed from the concentrated product. However, it should be appreciated that lignin separation can be carried out upstream of distillation.

In one embodiment of the invention, concentration of the still bottoms is carried out in an evaporator unit. The evaporation may be carried out in a single-stage evaporator or may be part of a multiple-effect system, i.e., a system in which more than one evaporator is employed. Multiple-effect evaporator systems are preferred as they can reduce heating requirements and the resultant energy usage. A multiple-effect evaporator system utilized in accordance with the invention can be forward fed, meaning that the feeding takes place so that the solution to be concentrated enters the system through the first effect, which is at the highest temperature. Partial concentration occurs in the first effect, with vapour sent to the second effect to provide heat for same. The partially concentrated solution is then sent to the second effect where it is again partially concentrated, with vapour sent to the third effect, and so on. Alternatively, backward feeding may be utilized, in which the partially concentrated solution is fed from effect to effect with increasing temperature.

Those of skill in the art can readily choose a suitable operating temperature for the evaporator unit. In embodiments of the invention, the operating temperature of the evaporator unit can be between about 40° C. and about 145° C., or any temperature therebetween. It will be understood that the temperature is measured at the operating pressure, which is typically under vacuum or at atmospheric pressure, but can be at higher pressure.

Salt Removal from Still Bottoms

Removal of salts from the still bottoms stream may be carried out by a variety of techniques including, but not limited to, chromatographic separation, ion exchange, solvent precipitation, drying, crystallization and freeze crystallization. Recovery of inorganic salt by ion exclusion and subsequent crystallization is described in co-owned U.S. Pat. No. 7,670,813 (Foody), which is incorporated herein by reference.

The salts that are recovered in the process may depend on the chemicals utilized in chemical pretreatment and the subsequent neutralization of the pretreated feedstock. By way of example, if sulfuric acid is employed during pretreatment and ammonia or ammonium hydroxide is used to neutralize the acid pretreated feedstock prior to enzymatic hydrolysis, ammonium sulfate will be produced. Furthermore, sulfuric acid reacts with the cations of the carbonate salts present in the feedstock during pretreatment to form calcium sulfate, magnesium sulfate, potassium sulfate and sodium sulfate. Other chemicals that can be used for pretreatment include sulfuric acid, sulfurous acid, sulfur dioxide, phosphoric acid, hydrochloric acid, hydrobromic acid, glycolic acid and trifluoric acetic acid.

Examples of salts that can be recovered from the still bottoms include sulfate salts, phosphate salts, chloride salts, bromide salts, glycolate salts, trifluoro acetate salts and oxylate salts.

According to one embodiment of the invention, the salts recovered include at least sulfate salts, phosphate salts or chloride salts. Typically, a mixture of salts will be recovered, including salts produced by neutralization of the pretreatment chemical and salts arising from anionic components of the feedstock, such as carbonates, chlorides and oxylates.

By the term "fertilizer", it is meant any composition useful as a fertilizer that comprises a salt or mixtures thereof derived from the feedstock and/or derived from one or more process chemicals added during the lignocellulosic conversion process.

Examples of salts that find value as a fertilizer include salts of sulfate, phosphate and chloride. Thus, the salts that are recovered may include at least one of potassium sulfate, magnesium sulfate, ammonium sulfate, potassium phosphate, magnesium phosphate, ammonium phosphate, potassium chloride, magnesium chloride and ammonium chloride. Mixed salts, including, but not limited to, struvite, may be recovered for fertilizer use as well.

In one embodiment of the invention, salts are recovered from the still bottoms by crystallization. The salts may be recovered by exploiting changes in solubility as process conditions such as temperature, pressure, pH, ionic strength and dielectric constant are changed.

Salt Removal by Solvent Precipitation

In one particularly advantageous embodiment, the precipitation is carried out by the use of a solvent. The solvent may be any suitable alcohol that alters the solubility of chemical compounds in water solution. Alcohols that may be used in accordance with the invention, include, but are not limited to, methanol, butanol, ethanol, propanol, isopropanol, or other aliphatic or aromatic alcohol that is soluble in water solution.

Addition of a suitable alcohol to a salt-containing stream generally reduces the solubility of the salts in the solution, and causes them to precipitate as insoluble solids, which may be removed from the stream by any of numerous methods well known to those skilled in the art. Suitable techniques for separation of the insoluble solids may include pressure or vacuum filters, centrifugal filters or centrifuges, membrane filtration systems, or gravity settlers. To increase the recovery of the salt, reduce the alcohol requirement, and improve the process economics, the still bottoms stream may be concentrated by any of several well known techniques, such as those described previously, prior to introduction of the alcohol stream.

Further, the liquid stream remaining after removal of the precipitated salts may be further processed to recover and recycle the alcohol used in the process. This may be carried out by distillation, pervaporation, or selective changes in solubility behavior induced by temperature, pH, ionic strength, pressure or other process conditions that can be altered. Without being limiting, a solvent recovery process is exemplified in FIG. 3.

Precipitation of the inorganic salts may be performed by mixing the still bottoms with the solvent at a suitable ratio in one or a series of crystallizers. By the term "crystallizer", it is meant any suitable device, such as a vessel, mixer, settler, or other suitable device, for carrying out precipitation of salts in the still bottoms stream.

The insoluble solids formed may be concentrated and/or dried by conventional techniques. The salt stream can then be used as a liquid fertilizer, or alternately dried and/or subjected to agglomeration and granulation for use as a solid fertilizer. Drying includes direct and indirect drying. Direct drying refers to using direct contact of hot gases to drive off some, or all of the water, and indirect drying refers to contact with a heated surface as opposed to hot gas.

The dried salts may be subjected to further processes such as agglomeration, compaction, granulation or mixing with other products to impart desired physical properties as required by the application.

Although alcohol addition to the still bottoms has been described above, it should be understood that the solvent may be added to a stream derived from the still bottoms. For example, the solvent can be added to a mother liquor obtained after precipitation of insoluble salt from the still bottoms by cooling and/or evaporation.

Incineration

The stream comprising lignin and the de-salted still bottoms stream are fed to an incinerator and the heat generated therein is utilized to produce steam, process heat, building heat, electricity generation, or any combination of these uses. By the term "incinerator" it is meant any suitable device for combusting these streams. By the term "de-salted still bottoms", it is meant a still bottoms stream or composition from which at least a portion of the salts have been removed therefrom.

Depending on the water content, the lignin may be conveyed to the incinerator via a screw conveyor or other device for conveying solids. The stream comprising lignin and de-salted still bottoms stream may be combined and then fed to the incinerator or each stream may be fed separately.

The incinerator may include a boiler section in which water or other fluid is heated. The heat produced from the burning of these streams is transferred to boiler feed water to produce steam. The furnace may be a fluidized bed boiler, although other types may be used as required. The feed to the boiler may also include bio-gas produced during anaerobic digestion. Moreover, during the start-up stage of the process, a small amount of natural gas may be added to the furnace to heat the fuel to the ignition point. Depending on the efficiency of salt removal and emissions regulations, exhaust from the furnace may be passed to a scrubber or other series of operations to reduce pollutant levels before being discharged to the environment. As well, particulate matter may need to be removed from the exhaust. Ash from the system may be landfilled or sold as an additional coproduct depending on its composition.

The steam may be used to drive turbines to create electricity for plant needs and/or can be sold to the power grid. Alternatively, or in addition to electricity generation, the steam can be used to supply process heat needs within the plant. If the steam is used within the plant, the pressure may be reduced prior to its re-use in the process. Examples of stages of the lignocellulosic conversion process to which steam can be supplied are pretreatment, fermentation, distillation, evaporation, fertilizer recovery and enzyme production. Furthermore, the steam can be utilized to provide building heating.

DETAILED DESCRIPTION OF THE PREFERRED EMBODIMENTS

The method of the present invention will be described by reference to the figures. It should be understood, however, that the figures shown are merely exemplary of apparatus suitable for carrying out the present invention and other equivalent means may be utilized without departing from the spirit of the invention.

Referring now to FIG. 1A, there is shown a non-limiting example of the process for generating steam and recovering salts during a lignocellulosic conversion process conducted in accordance with embodiments of the invention. As shown in FIG. 1A, comminuted feedstock is subjected to pretreatment 10 with sulfuric acid to hydrolyse xylan to xylose, glucose, arabinose, mannose and galactose. The cellulose in the acid pretreated feedstock is then hydrolysed by cellulase enzymes in hydrolysis 20 to produce glucose. The hydrolysate resulting from hydrolysis 20 is then fed to lignin separation 30 wherein the lignin is removed, along with other unconverted undissolved solids by a filter press that dewaters to a solids concentration of about 50-55 wt % to produce a filter cake. The hydrolysate from which lignin and other undissolved solids has been removed is then fed to fermentation 40 where xylose and glucose are converted to ethanol by a *Saccharomyces cerevisiae* yeast strain that is capable of converting both sugars to ethanol (see U.S. Pat. No. 5,789,210, incorporated herein by reference). The resultant ethanol-containing solution is fed to distillation 50 to concentrate the ethanol. Subsequently the ethanol-rich vapor is further concentrated by molecular sieves (not shown) to remove residual water. The still bottoms remaining after distillation are fed to evaporation 60 and concentrated to increase the total solids to a value that is suitable for solvent precipitation.

The evaporated still bottoms are then fed to a de-salting operation 70, which may include addition of a solvent, as shown in more detail in FIG. 2 and described below. After de-salting 70, the solvent is recovered in solvent recovery stage 80 and fed back to the de-salting 70 and the separated salts are processed further to make fertilizer. The organics remaining after solvent recovery are sent to a boiler 90 and incinerated therein. In addition, the lignin filter cake, containing lignin and other undissolved solids derived from the hydrolysate, from lignin separation 30 is conveyed to the boiler. The heat energy from incinerating both lignin and de-salted still bottoms in the boiler 90 is used to generate steam for use in the process and/or to generate electricity in a turbine.

Figure 1B:
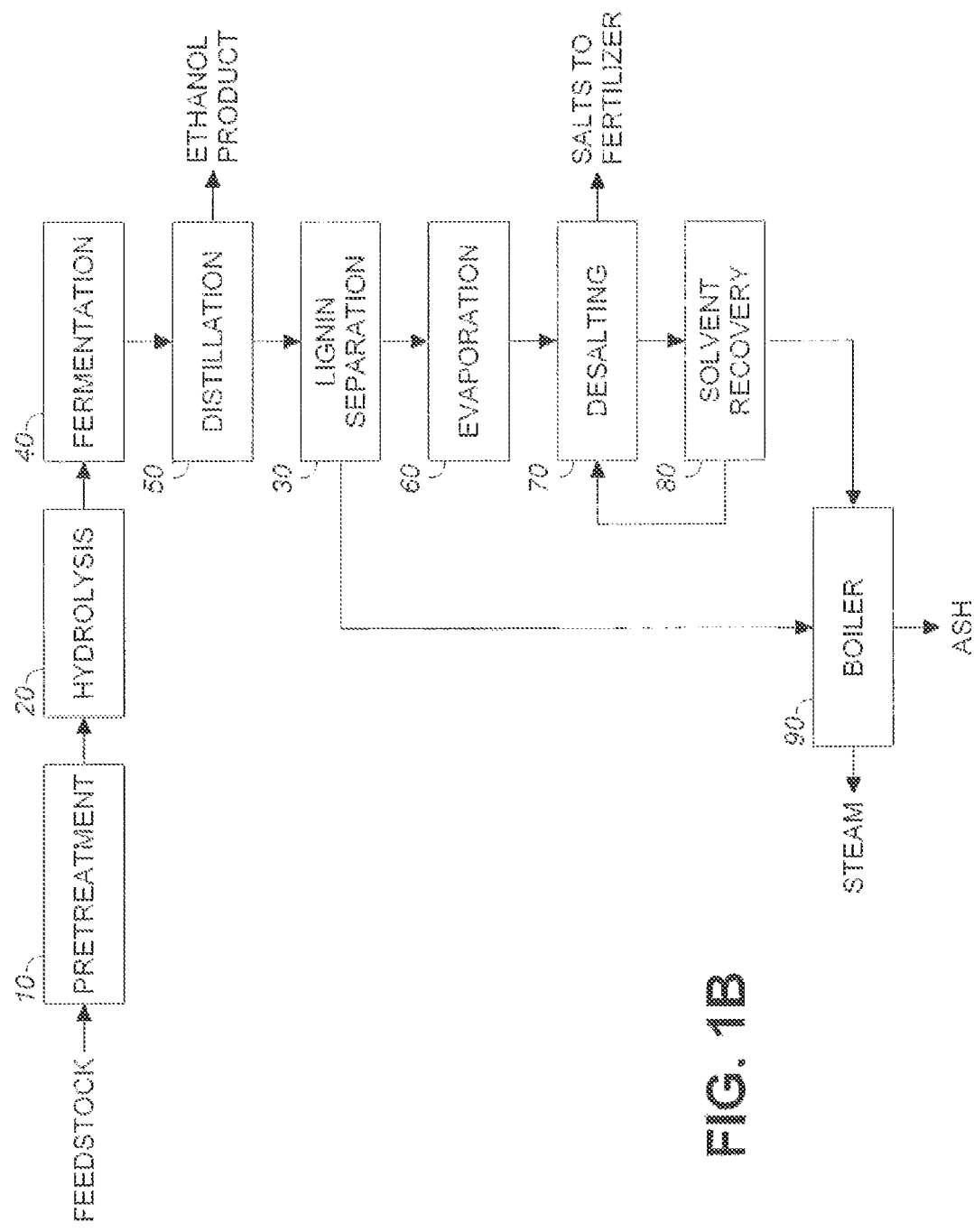
FIG. 1B is a process flow diagram depicting an embodiment of the invention in which a lignin stream is isolated after distillation and combined with a de-salted still bottoms stream to produce a combined stream that is combusted to generate steam.

FIG. 1B is similar to FIG. 1A except the lignin separation 30 is downstream of distillation 50. As shown in FIG. 1B, a hydrolysate resulting from pretreatment 10 and hydrolysis 20 is fed to fermentation 40 without a prior step of lignin separation. The resultant ethanol-containing solution containing insoluble lignin is fed to distillation 50 to concentrate the ethanol. Subsequently the ethanol-rich vapour is further concentrated by molecular sieves (not shown) to remove residual water. The still bottoms remaining after distillation 50 are subjected to lignin separation 30. The lignin filter cake, containing lignin and other undissolved solids derived from the lignin separation 30, is conveyed to the boiler 90. The clarified still bottoms from lignin separation 30 is fed to evaporation 60 and concentrated to increase the total solids to a value that is suitable for desalting 70 and solvent recovery 80. The desalted stream from solvent recovery 80 is routed to boiler 90.

Figure 2:
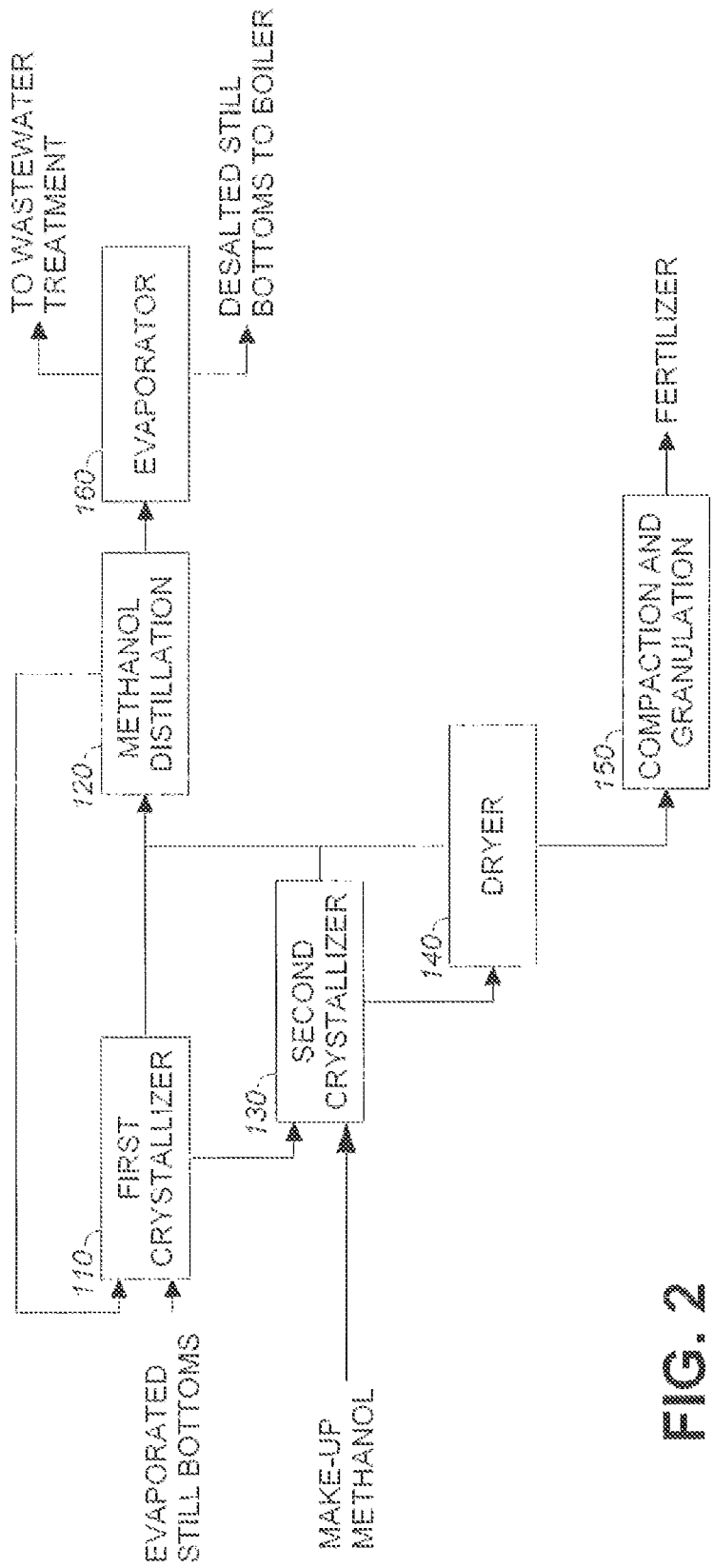
FIG. 2 is a process flow diagram depicting an embodiment of the invention in which a still bottoms stream is de-salted by precipitation with an alcohol.

Turning now to FIG. 2, there is shown a non-limiting example of the process for recovering salts by addition of solvent during a lignocellulosic conversion process conducted in accordance with embodiments of the invention. As shown in FIG. 2, an evaporated still bottoms, obtained from evaporation 60 (see FIGS. 1A and 1B) is fed to a first crystallizer 110. In the first crystallizer 110, the evaporated still bottoms is mixed in a suitable ratio, such as but not limited to, a 4:1 solvent-to-feed ratio (w/w) with recycled methanol recovered from a methanol still 120. The precipitated solids from the first crystallizer 110 are fed to a second crystallizer 130 fed with fresh, make-up methanol in suitable ratios, such as but limited to, a 1:1 ratio (w/w). The solids from the second crystallizer 130 are sent to a dryer 140 where the salts are concentrated, and subsequently sent to a stage of compaction and granulation 150 to produce fertilizer. The liquid from the first 110 and second 130 crystallizers and the dryer 140 are sent to the methanol still 120. The recovered methanol from the methanol still 120 is recycled to the first crystallizer 110, while the bottoms are concentrated to a level sufficient to support incineration in a two effect evaporator 160. Evaporator 160 produces a de-salted still bottoms stream, which is fed to the incinerator, in this case a boiler, and a waste stream that is fed to waste water treatment.

It should be appreciated that FIGS. 1A, 1B and 2 and the examples set forth below are for illustrative purposes only and should not be construed to limit the current invention in any manner.

EXAMPLES

Example 1

The Production of Inorganic Salt and a Lignin Byproduct from a Lignocellulosic Conversion Process The following example illustrates the origin of inorganic salts from a lignocellulosic conversion process that converts sugar to ethanol, by a process comprising pretreatment of a lignocellulosic feedstock, enzymatic hydrolysis of cellulose to produce glucose, fermentation of the glucose to ethanol and concentration of the ethanol by distillation. As outlined below, the inorganic salts arise from both alkali salts endogenous to the feedstock and from process chemicals added during the process. These salts are then carried through to a still bottoms stream that remains after concentration of the ethanol by distillation.

This example also describes the stages of the process where streams arise that comprise lignin as a predominant component.

In addition to cellulose, hemicellulose and lignin, the lignocellulosic feedstock contains many secondary components, present in quantities ranging from parts per million to a few percent of the mass of the material. The identity and quantity of these secondary components will vary with the type of feedstock, the soil and location conditions found at the farm-site, the type and quantity of chemical fertilizers used at the particular farm-site, and the amount of weathering that the feedstock experiences prior to entering the cellulosic ethanol process. In general, it is expected that the feedstock will contain from approximately 0.5 wt % to approximately 3.0 wt % total alkali metals and alkaline earth metals, composed of varying amounts of potassium, sodium, calcium, and other elements. The feedstock will also contain from approximately 1 wt % to approximately 5 wt % silica. Smaller amounts of iron, aluminum, phosphorus, chloride, and many other elements are also present.

The first step of the process involved size reduction of the feedstock. Wheat straw was received in bales measuring 3 feet by 3 feet by 4 feet and chopped to approximately ¼ inch in size. The straw was then mixed with water and sent to a standpipe where 93% (w/w) sulfuric acid was added to reduce the pH of the straw-water mixture to about 1.2, though other pH values ranging from pH 0.8 to about pH 3 can be utilized.

The slurry was pumped or otherwise conveyed through processing equipment heated by direct injection with 600 psig steam to reach a temperature of at least 170 C. The heated, acidified stock was held at this temperature for about 30 seconds up to about 5 minutes as it passed through the equipment. This hot, acidic cooking process is called acid pretreatment. A range of pH, temperature, and reaction times are possible when conducting acid pretreatment so long as conditions are sufficient to hydrolyze all or a significant portion of the hemicellulose to its monomeric constituents, including xylose, galactose, mannose, arabinose, acetic acid, galacturonic acid, and glucuronic acid.

Upon exiting the pretreatment process, the pretreated fibrous slurry was flashed through a series of cyclones to drop the temperature to approximately 85 C. The slurry was further cooled to approximately 50 C.

The slurry pH was then adjusted to pH 5.0 with concentrated aqueous ammonia solution. The addition of the aqueous ammonia solution neutralizes the acid used during the pretreatment process and thereby generates ammonium salts, primarily ammonium sulfate and ammonium acetate, in the pretreated fiber slurry. These salts contribute to the inorganic salt load carried through to the still bottoms.

While much of the hemicellulose is hydrolyzed to monomers during the pretreatment process, there is little conversion of the cellulose to glucose. The cellulose is hydrolyzed to glucose in a subsequent step that uses cellulase enzymes; this process is referred to as enzymatic hydrolysis. Enzymatic hydrolysis was conducted in a hydrolysis tank with a volume of approximately 100,000 liters. The tank was equipped with agitators to mix the slurry. The slurry consisted of approximate 18 wt % undissolved solids, and the undissolved solids consisted of 55% cellulose. Cellulase enzymes from *Trichoderma reesei* were used in the present example, although the enzyme mixture may be derived from other organisms. The enzyme dosage is typically 35 mg protein per gram cellulose, which corresponds to a cellulase activity of 35.6 Filter Paper Units (FPU) per gram of cellulose. The enzymatic hydrolysis reaction was completed over a period of a few days, at a temperature in the range of 40-65° C., at a pH in the range of 4-6. The pH may be adjusted continuously throughout the reaction period by use of a base, such as aqueous ammonia. The enzymatic hydrolysis typically was run until over 90% of the cellulose is converted to glucose.

At the completion of the reaction period, the resulting aqueous slurry contains unhydrolyzed fiber that is primarily lignin, and an aqueous solution of glucose, xylose, acetic acid, glucuronic acid, formic acid, lactic acid and galacturonic acid, ammonium salts, sulfate salts, and a variety of other ionic species. The final glucose concentration in the enzymatic hyrolysate was 120 g/L, the final xylose concentration was 59 g/L, the total solids was approximately 18 wt % and the total undissolved solids was approximately 8 wt %.

The hydrolysis slurry was filtered using a plate and frame filter press to separate the unhydrolyzed solid residue from the aqueous stream. The unhydrolyzed solid residue was deposited in the filtration apparatus as a filter cake which contains primarily lignin, unhydrolyzed cellulose and sand, with a small fraction of insoluble salts such as calcium sulfate. The filter cake was washed with water to remove more than 90% of the soluble compounds. The cake was compressed to remove water and, upon discharge, was at about 50 wt % undissolved solids. The filtration operation may also be conducted after the ethanol distillation process (discussed below) without affecting the composition of the lignin cake. Regardless of the position of the filtration operation within the overall flowsheet, the filter cake is conveyed to a boiler system for steam generation discussed below.

The aqueous process stream exiting the plate and frame filter press is essentially free of insoluble particles and contained glucose, xylose, and arabinose sugar; the soluble salts ammonium sulfate, ammonium acetate, potassium sulfate, magnesium sulfate and a small amount of dissolved calcium sulfate, and acetic acid, soluble lignin, other dissolved organics and other dissolved inorganic salts. This process stream was pumped to a fermentor vessel with a volume of approximately 90,000 liters. A *Saccharomyces cerevisiae* yeast strain from Purdue University that had been genetically modified to enable it to ferment xylose, as well as glucose, to ethanol (U.S. Pat. No. 5,789,210) was added. The sugar feed stream was added to the fermentor vessel over a period of 12 hours and then run in a batch fermentation mode for 48 hours. At the end of the fermentation, the yeast cells are separated from the fermentation broth (beer) and recycled back into the process.

The beer, which contains the ethanol product at approximately 11 wt %, was pumped to a carbon dioxide de-gas column and then to a continuous Coffey still. The first column in the still, a beer column, consisted of a number of perforated trays that permitted vapour, containing ethanol and other volatile components, to flow upwards from the bottom of the column to the top allowing for contact with the liquid flowing downwards from the top of the column to the bottom. This action allows the concentration of the volatile portions of the beer to become more concentrated as it moves from the bottom to the top of the column resulting in an ethanol concentration of approximately 40% alcohol by weight (abw). The overhead vapours from the beer column were fed to the bottom of a rectifying column where the ethanol concentration was further increased, although the concentration did not increase beyond the azeotrope point of 96% abw. From the top of the rectifying column, the vapours were pulled off with a fraction being condensed and returned to the top of the rectifying column via a reflux drum. The ethanol vapour was fed to a molecular sieve unit to complete the removal of water vapour, and then blended with gasoline to a final salable specification.

The residue remaining after distillation is a still bottoms stream that comprises a complex mixture of organics that are not consumed during the fermentation process and inorganic salts derived from the inorganic elements in the feedstock or added during the lignocellulosic conversion process to produce ethanol.

Example 2

The Combustion of Lignin and Concentrated Still Bottoms from a Lignocellulosic Feedstock without Salt Removal The following example serves to illustrate that the presence of inorganic salts, namely ammonia, ammonium and sulfate salts, derived from endogenous salts in the cellulosic ethanol feedstock and introduced as process chemicals during the production process can compromise the performance of combined incineration of still bottoms and lignin through the production of regulated pollutants or the formation of salt slags. In this example, the incineration is carried out in a fluidized bed boiler system. Production of regulated pollutants originating from the originating from the inorganic salts increases the cost and complexity of the boiler flue gas scrubbing system and may generate large quantities of chemical waste which requires handling, processing, and disposal. Furthermore, formation of salt slags may impede operation of a fluidized bed boiler system by causing bed agglomeration, excess bed material consumption, and possible unplanned shutdown due to bed collapse.

A still bottoms stream was obtained from the process as described in Example 1. The total solids content of this stream is typically 9-10 wt % total solids, with virtually no undissolved solids. The water content was lowered to allow for its use as a boiler fuel. This was carried out in a 4 stage multiple-effect evaporator to a target concentration of around 50 wt % total solids. The concentrated still bottoms was then fed to a boiler system as a fuel, generating steam for use in the plant or for the production of electricity. Ideally, the lignin rich filter cake and the concentrated still bottoms stream would be fed to the same boiler system to reduce the cost and complexity of running two separate boiler systems.

For the present example, the lignin rich filter cake was obtained from the filter press at 51 wt % total solids. The lignin rich filter cake had been washed thoroughly, so that the total soluble component content was about 1 wt %. The composition of the filter cake was 48 wt % water, 51 wt % solids, and 1 wt % miscellaneous soluble components. The solids were composed of about 79% lignin, 15% silica, 5% cellulose, and about 1% unidentified inorganic ash. Combustion analysis of the lignin yielded a higher heating value of 25,300 BTU/kg, dry basis.

The actual total solids of the concentrated still bottoms used in this example was 46.6 wt %. The composition of the concentrated still bottoms was 53.4 wt % water, 46.6 wt % soluble solids, and virtually no insoluble solids. The soluble solids were 48% organic, with unconsumed sugar, proteins and amino acids, soluble lignin, acetic acid, xylitol and other polyols comprising most of the organic mass. These organics form the valuable boiler fuel components of this stream. The balance of the soluble solids at 52% of the total solids were inorganic, and contained about 34% sulfate, 15.5% ammonium, 3.2% potassium, 0.15% sodium, 1.3% chloride, 1.3% phosphate, with the balance being composed of magnesium, calcium, and other un-quantified inorganic elements and compounds. The higher heating value for the concentrated still bottoms was measured to be 14,760 BTU/kg on a dry basis.

The ratio of concentrated still bottoms to lignin fed to the boiler system was 1.1:1 by weight. That is, 1.1 kg of concentrated still bottoms was fed for every 1 kg of wet lignin rich boiler cake. Combustion testing was run for three days under a variety of conditions, varying the bed temperature, excess air, air ratio staging, and use of selective non-catalytic reducing agents to control nitrogen oxides (NOx) formation. At times, lime was injected into the bed to absorb sulfur oxides (SOx). Samples of the fluidized bed sand was taken periodically and examined for evidence of agglomeration. Fly ash samples were taken periodically; the composition of the ash was measured via test method ASTM D4326, and the ash melting point was measured via ASTM D1857. Ash was further analyzed using differential thermal analysis (DTA) to determine if some fraction of the ash was melting prior to the bulk deformation observed in the ASTM D1857 test.

From the combustion results, on average, it was found that approximately 80% of the total sulfate fed to the boiler system decomposed into SOx, with the remainder forming thermodynamically stable sulfate salts at the temperature of the fluidized bed. The production rate of SOx species averaged around 201 kg of SOx per million BTU of fuel fed to the boiler system. Assuming a typical ratio of 1.6 kg calcium oxide per kg of SOx as an absorbent or scrubbing agent would mean that about 550 kg of mix calcium sulfate/calcium oxide waste would be generated per million BTU of fuel fed. This waste would likely have to be disposed of in an industrial landfill, presuming that no customer for the waste stream could be found co-located with the cellulosic ethanol plant. Furthermore, the NOx levels varied between 100 to 500 ppm in the flue gas stream, corrected to 3% excess oxygen, which far exceeds allowable emissions rates. Further flue gas clean-up using selective catalytic reduction (SCR) would be required, but was not investigated during this test.

The ash melting point determined via ASTM D1857 was around 900° C. for the initial deformation point, varying from a low of 810° C. to 1020° C. for the samples obtained. In general, this is similar to the expected operating temperature of a typical fluidized bed, with an expected operating temperature around 840° C. Differential thermal analysis indicated that around 15-25 wt % of the ash melted as a lower temperature, between 650-700° C., as indicated by an endothermic event not associated with a loss in mass. This suggests that at least a fraction of the ash is melting at a lower temperature, which may contribute to a "sticky" ash and foul heat exchange surfaces in the boiler system. The duration of the test was insufficient to determine the actual rate of ash build-up in the boiler system.

Example 3

Alcohol Precipitation of Inorganic Salts from the Concentrated Still Bottoms Stream The concentrated still bottoms stream described in Example 2 was subjected to an alcohol treatment process to precipitate the salts, and reduce the problems associated with the salts in the boiler system. At the laboratory scale, a 100 mL sample of concentrated still bottoms was mixed with methanol at room temperature; the volume ratio of concentrated still bottoms to methanol was 1:4 in this example, but other ratios and temperatures would give similar results. The mixture was allowed to stir for 10 minutes, and the precipitate that formed was filtered using a standard medium porosity sintered glass crucible. The collected solids were washed with a 100 mL of cold methanol to initial still bottoms, and the washings combined with the initial filtrate. The combined filtrates were evaporated in at 50° C. at reduced pressure in a standard laboratory roto-evaporator, until the concentrate volume was 100 mL, equal to the initial volume of still bottoms used in the experiment. Approximately 200 mL of water was added to the concentrate, and the evaporation process repeated to remove most of the methanol from the sample. The final de-salted, concentrated still bottoms was analyzed to determine organic content and concentration by species, inorganic content and concentration by species, and total solids. The precipitated material collected on the glass crucible was oven dried at 105° C. to constant mass and was analyzed to determine total organic content, inorganic content, and concentration by species.

The solvent precipitation process removed 85.5 wt % of the inorganic salts contained in the concentrated still bottoms, and removed only 10 wt % of the total organics. On a per inorganic species basis, 97.5 wt % of the potassium in the concentrated still bottoms was removed by the alcohol treatment, as was 75.6 wt % of the ammonium, 98.9 wt % of the sulfate, and 100 wt % of the calcium. Almost none of the sodium or chloride was removed by the alcohol treatment described. The removal of the 98.9 wt % of the sulfate would reduce the expected SOx in a boiler system to around 2.2 kg per million BTU of combined lignin and still bottoms fuel fed to the system, and the resultant mixed calcium oxide/calcium sulfate SOx scrubbing waste to around 6.0 kg per million BTU.

A portion of the desalted, concentrated still bottoms was dried at 105° C., and the residual solids ashed in a muffle furnace for 3 hours at 575° C. The ash produced from this treatment was analyzed via differential thermal analysis. The fraction of low temperature melt material in the 650-700° C. temperature range had been reduced to less than 5 wt % of the total ash.

Further, analysis of the precipitated material indicates that it could likely be processed to a salable fertilizer, or a blend component for established fertilizer manufacturing operations. Analysis via standard agronomy methods showed that the precipitated salt sample contained 11.8 wt % nitrogen, 10.9 wt % potassium, 19.0 wt % sulfur, 3.4 wt % hydrogen, 37.9 wt % oxygen, 1.3 wt % calcium, with the balance being unclassified organic. The nitrogen and potassium are typical fertilizer components that would be valuable in the marketplace. Preliminary root box studies at typically applied nitrogen and potassium ratios did not indicate any toxic effects; plant growth was comparable to a control commercial fertilizer product applied with similar nitrogen and potassium dosages.

The invention claimed is:

1. A process for generating steam and recovering salts during a lignocellulosic conversion process, said process comprising the steps of:
    obtaining a liquid-containing stream comprising lignin and a separate liquid still bottoms stream generated during the lignocellulosic conversion process;
    (ii) removing at least a portion of the water from the still bottoms stream to produce a liquid-containing concentrated still bottoms stream;
    (iii) removing at least a portion of the salts from the liquid concentrated still bottoms stream to produce a liquid-containing de-salted still bottoms stream;
    (iv) introducing both the liquid-containing stream comprising lignin and the liquid-containing de-salted still bottoms stream to an incinerator and incinerating the same; and
    (v) utilizing heat generated from said incinerating to produce steam.

2. The process of claim 1, wherein between about 10 and about 90% of the water is removed from the still bottoms stream to produce the concentrated still bottoms stream.

3. The process of claim 2, wherein between about 30 and about 90 wt % of the water is removed from the still bottoms stream to produce the concentrated still bottoms stream.

4. The process of claim 1, wherein the step of removing at least a portion of the salts from the concentrated still bottoms stream comprises precipitating salts from the concentrated still bottoms stream by addition of a solvent.

5. The process of claim 4, wherein the solvent is an alcohol.

6. The process of claim 5, wherein the alcohol is methanol, butanol, ethanol, propanol or isopropanol.

7. The process of claim 6, wherein the alcohol is methanol or ethanol.

8. The process of claim 6, wherein the alcohol is recovered and recycled.

9. The process of any claim 1, further comprising producing fertilizer from the salts removed from the concentrated still bottoms.

10. The process of claim 1, wherein said lignocellulosic conversion process comprises a step of enzymatic hydrolysis to produce glucose from cellulose and thereafter conducting a lignin separation process on a hydrolysate stream resulting from said enzymatic hydrolysis, thereby providing said stream comprising lignin.

11. The process of claim 10, wherein the lignin separation process utilizes a filter press.

12. The process of claim 1, wherein said lignocellulosic conversion process comprises a step of fermentation to produce a fermentation product and thereafter conducting a lignin separation process on a fermentation beer stream, thereby providing said stream comprising lignin.

13. The process of claim 12, wherein the fermentation produces ethanol.

14. The process of claim 12, wherein said lignocellulosic conversion process comprises a step of fermentation to produce a fermentation product and thereafter conducting a lignin separation process on a still bottoms stream thereby providing said stream comprising lignin.

15. The process of claim 14, wherein the fermentation produces ethanol.

16. The process of claim 1, wherein the incinerator is a boiler.

17. The process of claim 16, wherein the boiler comprises a bubbling fluidized bed.

18. The process of claim 1, wherein the step of removing water from the still bottoms comprises evaporation.

* * * * *

UNITED STATES PATENT AND TRADEMARK OFFICE
CERTIFICATE OF CORRECTION

| | | |
|---|---|---|
| PATENT NO. | : 9,102,951 B2 | Page 1 of 1 |
| APPLICATION NO. | : 14/241133 | |
| DATED | : August 11, 2015 | |
| INVENTOR(S) | : Robert Griffin et al. | |

It is certified that error appears in the above-identified patent and that said Letters Patent is hereby corrected as shown below:

Specification

COLUMN 19:

Line 29, "obtaining" should read --(i) obtaining--.

Claims

COLUMN 20:

Line 15, Claim 9, "any" should be deleted.

Signed and Sealed this
Fifth Day of April, 2016

Michelle K. Lee
*Director of the United States Patent and Trademark Office*